United States Patent
Bennett-Guerrero et al.

(12) 
(10) Patent No.: US 6,365,128 B1
(45) Date of Patent: *Apr. 2, 2002

(54) MONITORING GASTROINTESTINAL FUNCTION TO GUIDE CARE OF HIGH RISK PATIENTS

(75) Inventors: Elliott Bennett-Guerrero, New York, NY (US); Michael G. Mythen, London (GB)

(73) Assignee: Medical Defence Technologies, LLC, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/464,261

(22) Filed: Dec. 17, 1999

Related U.S. Application Data

(60) Provisional application No. 60/112,901, filed on Dec. 18, 1998.
(51) Int. Cl.$^7$ .............................................. A61K 49/00
(52) U.S. Cl. ........................ 424/9.2; 424/1.11; 424/9.1
(58) Field of Search ............................... 206/223, 569, 206/570; 374/209; 600/9, 300, 309, 11; 424/1.11, 9.1, 9.2

(56) References Cited

U.S. PATENT DOCUMENTS 4,381,011 A * 4/1983 Somers, 3rd ................ 128/635
5,500,430 A * 3/1996 Makovec et al. ........... 514/278
5,690,960 A * 11/1997 Bengtsson et al. .......... 424/480

OTHER PUBLICATIONS

Calvet et al, Intensive Care Med., 1997, vol. 23, pp. 738–742.*
Mohsenifar et al, Ann. Intern. Med., 1993, vol. 119, pp. 794–798.*
Calvet et al, Intensive Care Med., 1998, vol. 24, pp. 12–17.*
Carmel, *Digestive Diseases and Sciences,* vol. 30, No. 12, pp. 2516–2522, "In Vitro Studies of Gastric Juice in Patients with Food–Cobalamin Malabcorption", Dec. 1994.*
Estevens et al, *Gastroenterology,* vol. 108, No. 4, p. A464, "The Importance of Gastric Juice pH in Maintenance of Intragastric Environment", Apr. 1995.*
Carmel, In Vitro Studies of Gastric Juice in Patients with Food–Cobalamin Malabsorption, Digestive Diseases and Science 39:2516–2522 (1994).

* cited by examiner

*Primary Examiner*—Dameron Jones
(74) *Attorney, Agent, or Firm*—Fish & Richardson P.C.

(57) ABSTRACT

A method of guiding the care of a critically ill patient or other high risk patient, said method comprising administering an effective dose of a gastric acid stimulant or suppressant agent and then measuring for an acute change in the gastric juice pH. A patient who demonstrates a significant change in the gastric juice pH using this test can have their medical care normalized in an accelerated fashion thereby reducing the duration, intensity, and cost of their care. Conversely, a patient who is not responsive is not ready for reduced support and may require more support.

10 Claims, No Drawings

MONITORING GASTROINTESTINAL FUNCTION TO GUIDE CARE OF HIGH RISK PATIENTS

RELATE APPLICATION

This application claims the benefit of U.S. Provisional Application No. 60/112,901, filed Dec. 18, 1998.

BACKGROUND OF THE INVENTION

Many patients receive care in an intensive care unit or similar setting following surgery, injury, trauma, or acute medical illness. At some time in their disease course they may suffer from dysfunction or failure of one or more organ systems. Although some patients succumb from their illness and die, most eventually recover, albeit after a prolonged duration of hospitalization.

Decisions must be made about whether and when patients are ready for a normalization (or accelerated normalization) of their care. Several types of common clinical problems are exemplified below:

Initiation of Enteral Feeding

Enteral feeding, i.e. instilling food into the stomach or intestines via a feeding tube or the mouth, is beneficial to some patients but deleterious to those patients whose gastrointestinal perfusion and function is suboptimal. Failures in enteral feeding can be classified as either "underfeeding" or "overfeeding". Underfeeding results when a critically ill patient is either not started on enteral feeds or else is administered suboptimal calories. Underfeeding can result in malnutrition and its associated complications (e.g. infections, low colloid oncotic pressure) which results in a prolongation of the duration of ICU stay and hospitalization. Overfeeding, in contrast, results when a patient is enterally fed but the patient's gastrointestinal tract (or overall circulatory system) is not yet healthy enough to tolerate the increased stress of enteral feeding. Overfeeding can result in vomiting and aspiration of enteral feeds into the lungs leading to aspiration pneumonitis/pneumonia. Overfeeding can also lead to ileus, fever, and abdominal tenderness which can mimic other serious disorders such as abdominal abscess/infection, and dead bowel. It can be difficult to predict a priori which patients will tolerate enteral feeding.

Weaning from Mechanical Ventilation

Mechanical ventilation is used to support adequate oxygenation and ventilation in patients with pulmonary dysfunction. Providing mechanical ventilation to a patient when it is not necessary can lead to recognized complications such as muscle weakness and aspiration pneumonia and results in increased hospital length of stay. Discontinuing or weaning mechanical ventilation in a patient prematurely can lead to complications such as pulmonary failure, intestinal dysfunction, cardiac arrhythmias, and a general setback in the patient's recovery. It can be difficult to predict a priori whether patients require more or less ventilatory support.

Weaning of Vasoactive Medications

Vasoactive agents such as epinephrine, dobutamine, dopamine, norepinephrine, and milrinone are commonly administered to critically ill patients in order to insure adequate perfusion of vital organs. Unnecessary administration of these agents can result in prolonged hospitalization and the risk of complications such as cardiac arrhythmias. In contrast, insufficient administration of these agents can result in inadequate organ perfusion which can result in organ dysfunction and death. It can be difficult to determine if and how rapidly vasoactive agents can be weaned. It is also difficult to determine if circulatory support with vagoactive agents should be increased.

SUMMARY OF INVENTION

The present invention is a method of guiding the care of a critically ill patient or other high risk patient in which the response of gastric juice pH to an effective dose of a gastric acid stimulant or suppressant agent is used. Preferably the agent is a stimulant. A patient who demonstrates a significant change in the gastric juice pH using this test can have their medical care normalized in an accelerated fashion thereby reducing the duration, intensity, and cost of their hospital care. Conversely, a patient who fails to respond is not ready for normalization of care and may require an increased level of care. The invention provides a single objective test which simplifies care decisions.

The invention also features kits for guiding care of an acutely ill or high risk patient. The kits include at least one effective dose of a gastric acid stimulant or suppressant agent and apparatus providing access to the patient's gastric juice pH, such as a disposable gastric pH probe. Preferably the agent is a stimulant.

Other features and advantages of the invention will be apparent from the following description of the preferred embodiments.

DESCRIPTION OF INVENTION/PREFERRED EMBODIMENTS

A method of guiding the care of a critically ill patient or other high risk patient, said method comprising administering an effective dose of a gastric acid stimulant or suppressant agent and then measuring for an acute change in the gastric juice pH. The ability of the gastric cells to respond to this pharmacological challenge is a good indicator of the perfusion and function of the gastrointestinal tract. In contrast to the prior art which has described a pharmacological test for use in the diagnoses of chronic illnesses and rare endocrine disorders, this invention relates to the use of this challenge test to guide the care of patients with acute critical illness. Surprisingly, this test allows for the monitoring of organs unrelated to gastric acid secretion or suppression per se.

Target Population

Any patient with acute illness may benefit from this invention. Patients who are receiving care in an intensive care unit or similar setting following surgery, injury, trauma, or acute medical illness are likely candidates. In particular, patients with acute organ failure are at risk for inadequate gastrointestinal perfusion and dysfunction and are candidates for use of this method. Patients in whom decisions need to be made regarding either initiating or weaning enteral feeding, vasoactive agents, and/or mechanical ventilation may benefit from the use of the method described herein. The patients face acute medical situations, in which their condition may be changing and appropriate changes in medical treatment may be required.

Uses

Some of the uses of this test include assessing gastrointestinal perfusion and function in order to (among other things):

A. Guide the decision to extubate and/or wean a patient from mechanical ventilation (i.e. decrease ventilating support); or to increase ventilating support B. Guide the decision to initiate, increase, terminate, or wean enteral feeding;

C. Guide the decision to initiate, increase, terminate, or wean vasoactive agents.

Pharmacological Challenge Agents

It is preferable to use a gastric acid stimulant if the baseline gastric juice pH is greater than 2.0. It is preferable to use a gastric acid suppressant if the baseline gastric juice pH is less than 2.0. A positive signal is typically manifested by a change in several pH units from the baseline value although a change of 1.0 pH units in response to the challenge agent is usually indicative of a positive signal. Most patients respond in a clear way to the challenge which reduces ambiguity in the interpretation of the results. In the event of an ambiguous test in a patient with a baseline pH of 2–3, it may be useful to repeat the test using the opposite pharmacological agent. For example, if pentagastrin is initially used and yields a negative response it may be useful to subsequently conduct a challenge test with omeprazole, preferably allowing at least 1–3 hours in between tests. A pharmacological challenge is typically conducted once every 1–3 days, although more frequent measurements can be made if deemed useful. If the patient is receiving enteral nutrition it may be preferable to discontinue feeding for several hours (e.g. 4 hrs.) prior to a pharmacological challenge.

Although any type of gastric acid stimulant can be used, the preferred agent is pentagastrin, a commercially available agent. Pentagastrin is a synthetic pentapetide that contains the carboxyl terminal tetrapeptide responsible for the actions of natural gastrins and its most prominent action is in the stimulation of gastric acid secretion. Pentagastrin stimulates gastric acid secretion approximately 10 minutes after subcutaneous injection with peak response occurring in most cases 20–30 minutes after administration. The duration of activity is usually between 60–80 minutes. Pentagastrin has a short half life of approximately 10 minutes. The preferred route of administration is subcutaneous although any alternative route, e.g. intravenous, may be acceptable. Any dose which has no significant side effects and is effective at stimulating gastric acid secretion can be used. The typical dose of pentagastrin is 6 micrograms/kg for subcutaneous administration.

Any acute acting gastric acid suppressant can be used. Example of useful gastric acid suppressants include proton pump inhibitors (e.g. omeprazole) and histamine H2 receptor antagonists (e.g. ranitidine). Proton pump inhibitors may be preferable given their direct mechanism of action. The preferred dosage and route of administration for the gastric acid suppressant will be relatively free of side effects and result in a significant pharmacological effect within 1 hour of administration. Examples of doses include omeprazole (80 mg intravenous) or ranitidine (50 mg intravenous).

Measurement of Gastric Juice pH

Any accurate method of measuring gastric juice pH may be used in this test. A method is preferable if it is easy to use, inexpensive, and relatively non-invasive and free of side effects. A preferred method involves the use of a pH measuring device that is encapsulated into the distal end of a standard 18 French tube that is inserted into the gastric lumen either through the mouth or nose. This tube would allow for the drainage of stomach contents, if necessary for other medical reasons, and administration of enteral feeds into the stomach, if feeding is deemed to be warranted. An example of such a tube is the GrapHprobe™ (Zinetics Medical, Utah, USA). A graphometer pH meter (e.g. Zynetics Medical, Utah, USA) can be connected to the sensor. This unit has a liquid crystal display and produces a measurement of gastric juice pH accurate to 0.1 pH unit. Alternative manufacturers of pH containing probes and pH monitors can be used.

EXAMPLE 1

(Prior Art)

A 70 year old patient develops severe pneumonia requiring admission to an intensive care unit, intubation of the trachea, and mechanical ventilation. After 3 days of illness enteral feeding is started. 2 days later enteral feeding is stopped as her abdomen has become swollen and tender and there is a suspicion that she may have aspirated gastric contents. The following day (6th day of illness) her respiratory support has to be increased. On day 9 of her illness enteral feeding is restarted successfully. By day 14 she is beginning to wean from the ventilator but once again her abdomen becomes swollen and tender so feeding is stopped. Weaning continues but is unsuccessful and by day 21 she is back on full respiratory support and receiving total parenteral nutrition. On day 25 she develops bacteremia from an infection of her intravenous feeding line. The line is removed and broad spectrum antibiotics are started. By day 32 she is again being fed enterally and is slowly weaning from the ventilator. On day 45 she is discharged from the ICU having made a complete recovery.

EXAMPLE 2

(Same Patient but now Shows use of Gastric Stimulation Test)

A 70 year old patient develops severe pneumonia requiring admission to an intensive care unit, intubation of the trachea, and mechanical ventilation. After 3 days of illness it is decided that she would benefit from enteral nutrition. A GrapHprobe™ (Zinetics Medical, Utah, USA) is inserted into the gastric lumen and connected to a graphometer pH meter (e.g. Zynetics Medical, Utah, USA). The baseline gastric juice pH is 5.4 and shows no change 20 minutes after the administration of pentagastrin 6 micrograms/kg subcutaneously. Attempts at feeding or weaning from the ventilator are postponed. One day later (day 4) the baseline gastric juice pH is 6.2 and again shows no change 20 minutes after the administration of pentagastrin 6 micrograms/kg subcutaneously. Additional intravenous fluids and a low dose of intravenous Dobutamine are given in an attempt to improve splanchnic perfusion. On day later (day 5) the baseline gastric juice pH is 5.9 and decreases to 1.8, 20 minutes after the administration of pentagastrin 6 micrograms/kg subcutaneously. Based on this positive challenge test enteral feeding is initiated and is well tolerated by the patient. The patient gains strength and by day 14 the dobutamine has been stopped and she is beginning to wean from the ventilator. On day 17 she is weaned from the ventilator. On day 18 she is discharged from the ICU having made a complete recovery.

What is claimed is:

1. A method of determining whether to initiate, terminate or modify a patient's medical intervention, the intervention comprising one or more supports selected from the group consisting of: a) mechanical ventilation of said patient, b) enteral feeding of said patient, and c) intravenous administration of one or more vasoactive agents, said method comprising, a) administering an effective dose of a gastric acid stimulant or suppressant agent to the patient;

b) measuring a change in the patient's gastric juice pH of at least 1.0 pH unit responsive to said dose; and c) either terminating, failing to initiate, or reducing said support based at least in part on said change in gastric juice pH, or initiating, maintaining, or increasing said support based at least in part on the absence of said change.

2. A method as in claim 1 in which the gastric acid stimulant agent is pentagastrin.

3. A method as in claim 2 in which the dose of pentagastrin is 6 micrograms/kg given subcutaneously.

4. A method as in claim 1 in which the gastric acid suppressant agent is omeprazole.

5. A method as in claim 4 in which the dose of omeprazole is 80 mg given intravenously.

6. The method of claim 1 in which the support is administration of a vasoactive agent selected from the group consisting of: epinephrine, dobutamine, dopamine, norepinephrine, and milrinone.

7. The method of claim 1 in which the support is enteral feeding of said patient.

8. The method of claim 1 in which the support is mechanical ventilation of said patient.

9. A kit for determining whether to initiate, terminate, or modify a patient's medical intervention, the intervention comprising one or more supports selected from the group consisting of: a) mechanical ventilation, b) enteral feeding, and c) administration of vasoactive agents, said kit comprising at least one effective dose of a gastric acid stimulant or suppressant agent and tubing providing access to the patient's gastric juice pH.

10. The kit of claim 9 wherein said tubing comprises a disposable gastric probe.

* * * * *

UNITED STATES PATENT AND TRADEMARK OFFICE
CERTIFICATE OF CORRECTION

PATENT NO.         : 6,365,128 B1
APPLICATION NO. : 09/464261
DATED                 : April 2, 2002
INVENTOR(S)       : Elliott Bennett-Guerrero and Michael G. Mythen It is certified that error appears in the above-identified patent and that said Letters Patent is hereby corrected as shown below:

Title page, (73) Assignee, "Medical Defence Technologies, LLC" should be
-- Medical Defense Technologies, LLC --.

Signed and Sealed this

Fourteenth Day of April, 2009

JOHN DOLL
*Acting Director of the United States Patent and Trademark Office*